(12) United States Patent
Wang

(10) Patent No.: US 11,423,455 B2
(45) Date of Patent: Aug. 23, 2022

(54) METHOD FOR DETERMINING A DESIGN OF A CUSTOMIZED FOOTWEAR OBJECT

(71) Applicant: CHAEI HSIN ENTERPRISE CO., LTD., Taichung (TW)

(72) Inventor: Shui-Mu Wang, Taichung (TW)

(73) Assignee: CHAEI HSIN ENTERPRISE CO., LTD., Taichung (TW)

(*) Notice: Subject to any disclaimer, the term of this patent is extended or adjusted under 35 U.S.C. 154(b) by 125 days.

(21) Appl. No.: 17/023,213

(22) Filed: Sep. 16, 2020

(65) Prior Publication Data

US 2021/0256585 A1 Aug. 19, 2021

(30) Foreign Application Priority Data

Feb. 19, 2020 (TW) ................................ 109105353

(51) Int. Cl.
*G06Q 30/06* (2012.01)
*G06F 30/10* (2020.01)
(Continued)

(52) U.S. Cl.
CPC ....... *G06Q 30/0621* (2013.01); *A43D 119/00* (2013.01); *G06F 30/10* (2020.01);
(Continued)

(58) Field of Classification Search
CPC .......... G06Q 30/0621; G06Q 10/0875; G06Q 30/0185; G06Q 30/0635; G06Q 50/04;
(Continued)

(56) References Cited

U.S. PATENT DOCUMENTS

2009/0287452 A1* 11/2009 Stanley .................. A43D 1/025
702/155
2018/0129763 A1 5/2018 Liang et al.
(Continued)

FOREIGN PATENT DOCUMENTS

CN 108510190 A 9/2018
JP 2017-131630 A 8/2017
(Continued)

OTHER PUBLICATIONS

Search Report, which was issued to European counterpart Application No. 20212090.3 by the EPO dated May 26, 2021 (10 pages).
(Continued)

*Primary Examiner* — Daniel A Hess
(74) *Attorney, Agent, or Firm* — Hamre, Schumann, Mueller & Larson, P.C.

(57) ABSTRACT

A method for determining a design of a customized footwear object for a wearer is provided. The method includes steps of: receiving a user input of a requirement data set regarding features that are related to the wearer; obtaining a cushion data set for producing a cushion of the footwear object based on the requirement data set, the cushion data set including data regarding a position of the cushion, data regarding a shape of the cushion, data regarding a material for the cushion and data regarding a hardness of the cushion; generating an order for production of the footwear object, the order including the cushion data set; and providing the order to a forming machine in order for the forming machine to produce the footwear object.

8 Claims, 10 Drawing Sheets

(51) Int. Cl.

| | |
|---|---|
| *A43D 119/00* | (2006.01) |
| *G06K 7/14* | (2006.01) |
| *G06K 19/06* | (2006.01) |
| *G06Q 10/08* | (2012.01) |
| *G06Q 30/00* | (2012.01) |
| *G06Q 50/04* | (2012.01) |
| *G06F 119/18* | (2020.01) |
| *A61B 5/11* | (2006.01) |

(52) U.S. Cl.
CPC ..... *G06K 7/1413* (2013.01); *G06K 19/06028* (2013.01); *G06Q 10/0875* (2013.01); *G06Q 30/0185* (2013.01); *G06Q 30/0635* (2013.01); *G06Q 50/04* (2013.01); *A61B 5/112* (2013.01); *G06F 2119/18* (2020.01)

(58) Field of Classification Search
CPC ..... G06F 30/10; A43D 119/00; G06K 7/1413; G06K 19/06028
USPC .......................................................... 703/1
See application file for complete search history.

(56) References Cited

U.S. PATENT DOCUMENTS

| | | |
|---|---|---|
| 2019/0216170 A1 | 7/2019 | Bischoff et al. |
| 2019/0261735 A1 | 8/2019 | Wawrousek et al. |
| 2019/0297995 A1 | 10/2019 | Loveder et al. |

FOREIGN PATENT DOCUMENTS

| | | |
|---|---|---|
| TW | 200733908 A | 9/2007 |
| TW | M419436 U1 | 1/2012 |
| WO | 2017/182930 A2 | 10/2017 |
| WO | 2019/124132 A1 | 6/2019 |

OTHER PUBLICATIONS

Search Report appended to an Office Action, which was issued to Taiwanese counterpart application No. 109105353 by the TIPO dated Jun. 12, 2020, with an English translation thereof (2 pages).
Office Action issued to Japanese counterpart application No. 2021-002775 by the JPO dated Dec. 21, 2021, with an English translation thereof (9 pages).

\* cited by examiner

METHOD FOR DETERMINING A DESIGN OF A CUSTOMIZED FOOTWEAR OBJECT

CROSS-REFERENCE TO RELATED APPLICATION

This application claims priority of Taiwanese Invention Patent Application No. 109105353, filed on Feb. 19, 2020.

FIELD

The disclosure relates to a method for determining a design of a customized footwear object.

BACKGROUND

Referring to FIG. 1, Taiwanese Utility Model Patent No. M419436 discloses a shoe 1 having a sole 11 and a cushion 12 embedded in the sole 11. The cushion 12 is made of an elastic material for absorbing shocks.

However, features of shoe-wearers, such as weight, height, foot type, foot size, and walking profile, even the activities (e.g., sports and exercises) that the shoe-wearers intend to perform with the shoes on, are all different, and thus standardized cushions of shoes may not be suitable for all the wearers.

SUMMARY

Therefore, an object of the disclosure is to provide a method for determining a design of a customized footwear object to be implemented using an electronic device that can alleviate at least one of the drawbacks of the prior art. The footwear object is customized for a wearer, and has a substrate and a cushion embedded in the substrate.

According to one aspect of the disclosure, the method includes steps of:

receiving a user input of a requirement data set regarding features that are related to the wearer;

obtaining a cushion data set for producing the cushion of the footwear object based on the requirement data set, the cushion data set including at least one of data regarding a position of the cushion, data regarding a shape of the cushion, data regarding a material for the cushion, or data regarding a hardness of the cushion;

generating an order for production of the footwear object, the order including the cushion data set; and providing the order to a forming machine in order for the forming machine to produce the footwear object.

According to another aspect of the disclosure, the method is for fabricating a customized footwear object to be implemented by an electronic device and a forming machine. The method includes steps of:

receiving, by the electronic device, a user input of a requirement data set regarding features that are related to the wearer;

obtaining, by the electronic device, a cushion data set for producing the cushion of the footwear object based on the requirement data set, the cushion data set including at least one of data regarding a position of the cushion, data regarding a shape of the cushion, data regarding a material for the cushion, or data regarding a hardness of the cushion;

generating, by the electronic device, an order for production of the footwear object, the order including the cushion data set;

providing, by the electronic device, the order to the forming machine; and forming, by the forming machine, the substrate and the cushion according to the order, wherein the cushion is embedded into the substrate at a position according to the data regarding the position of the cushion.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
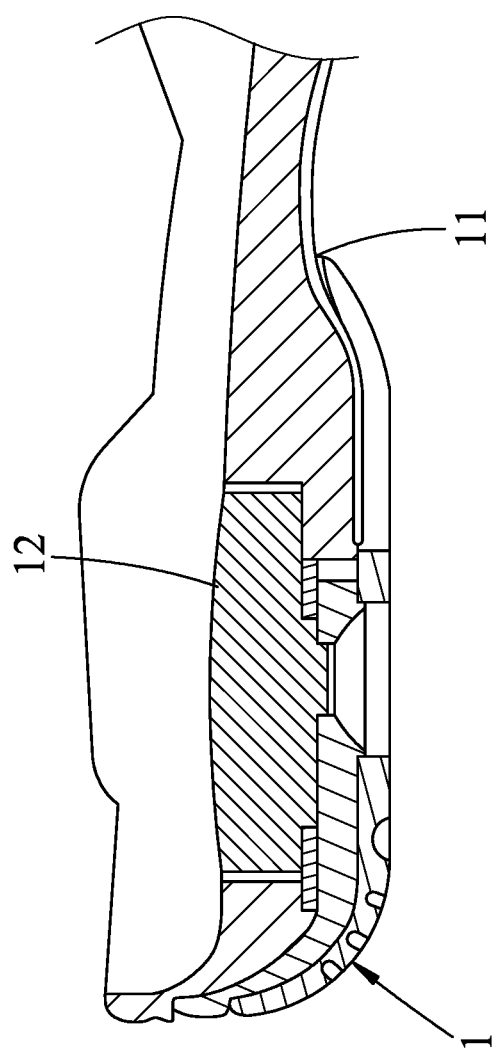
FIG. 1 is a sectional view of a part of a conventional shoe disclosed in Taiwanese Utility Model Patent No. M419436.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
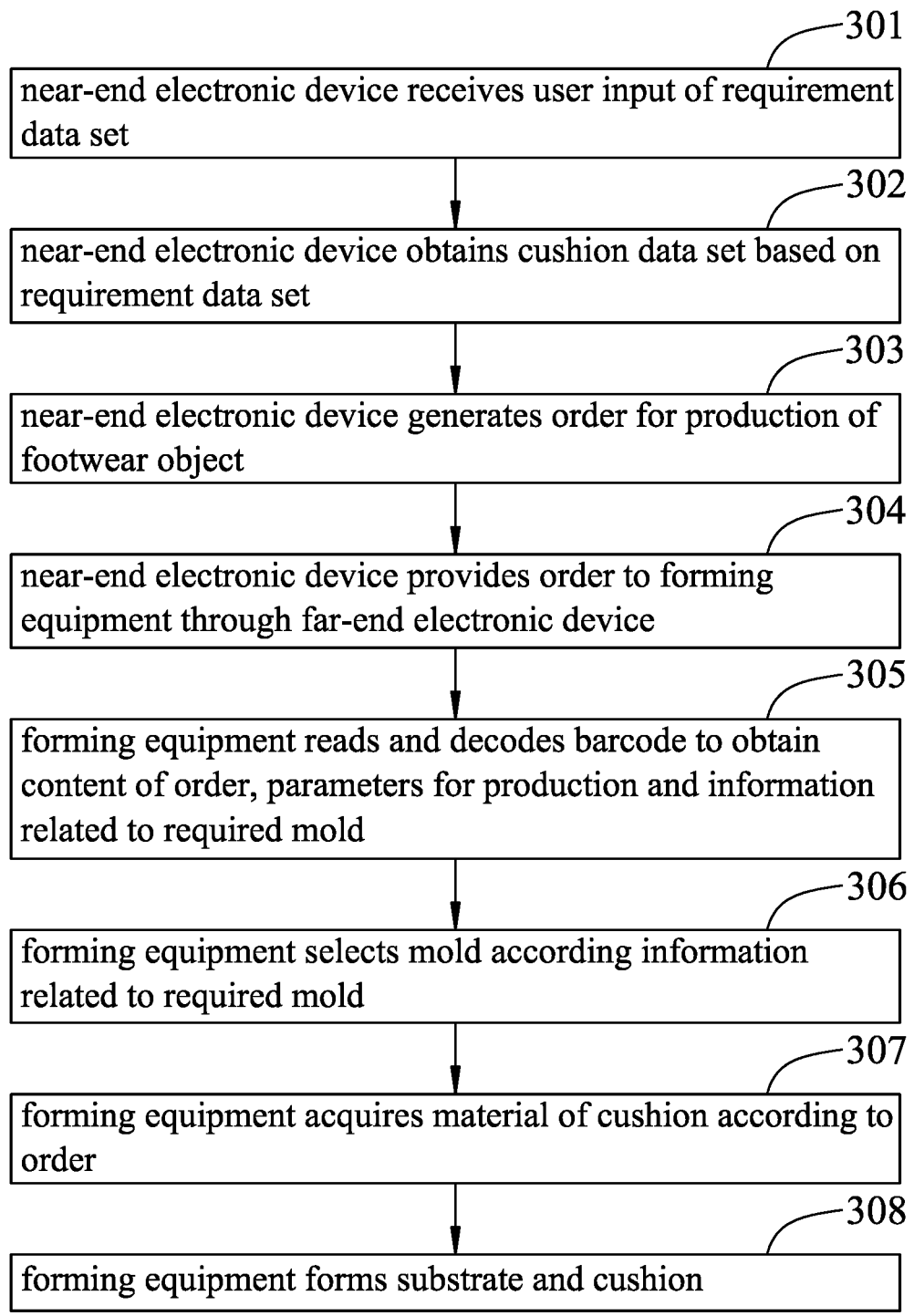
FIG. 2 is a flow chart of a method for determining a design of a customized footwear object according to an embodiment of the disclosure.
Figure 10:
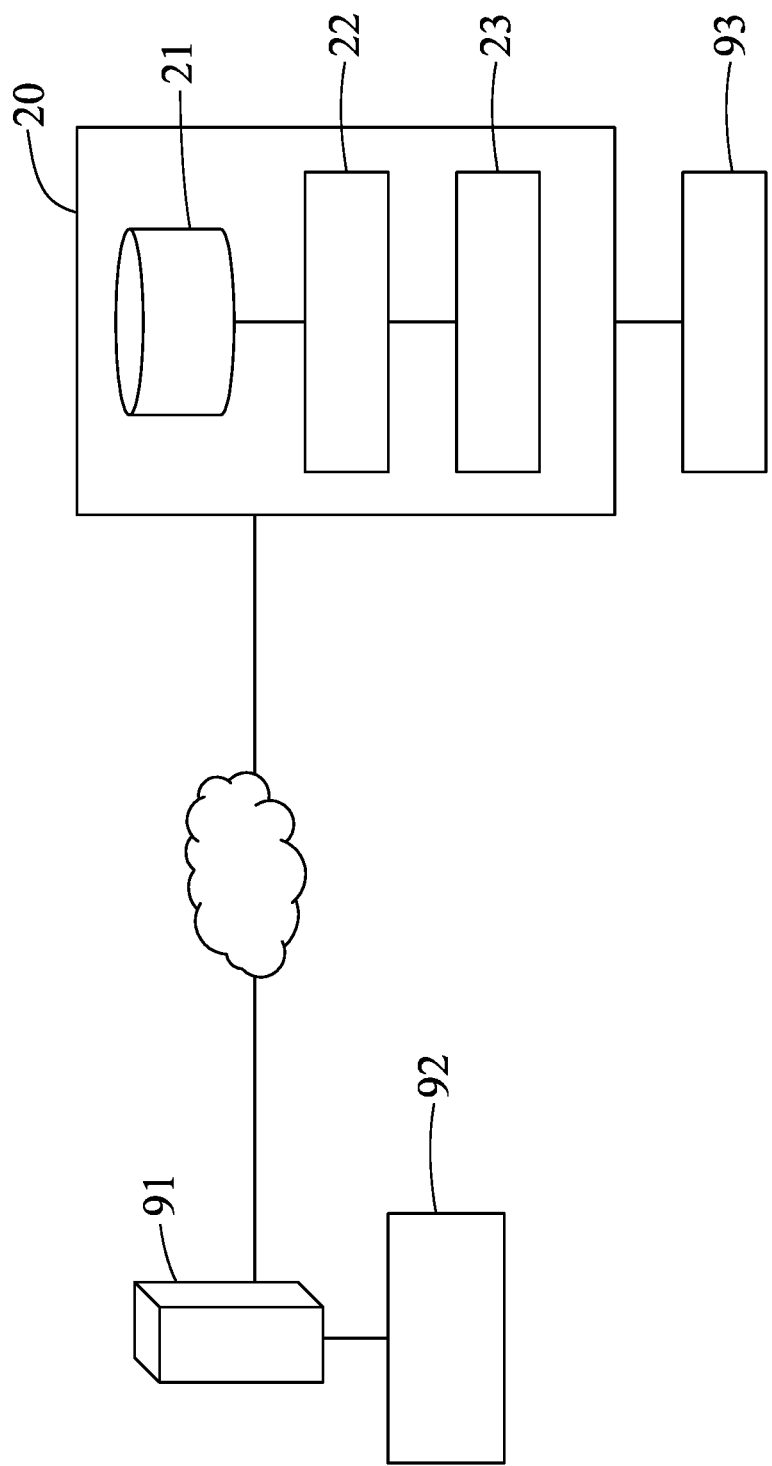
FIG. 10 is a schematic diagram illustrating electronic devices and a forming machine used to perform the method for determining a design of a customized footwear object according to an embodiment of the disclosure.

Referring to FIGS. 2 and 10, a method for determining a design of a customized footwear object according to an embodiment of this disclosure is implemented using a near-end electronic device 20, a far-end electronic device 91 and a forming machine 92.

The near-end electronic device 20 may be any general-purpose computing device, such as, but not limited to, a point-of-sale (POS) system, a personal computer, a notebook computer, a tablet, a smartphone, etc. The far-end electronic device 91 may be a cloud-based platform, a remote server, or a computing device that is placed at a factory where the forming machine 92 is located. The far-end electronic device 91 is configured to communicate with the forming machine 92, and the near-end electronic device 20 is configured to communicate with the far-end electronic device 91, for example, over the Internet. The near-end electronic device 20 may, in some embodiments, be operated by the staff of a retail store or a customer for receiving user inputs. In further embodiments, the near-end electronic device 20 and the far-end electronic device 91 are integrated into a single computing device that is configured to be operated by the staff of the retail store or the customer, and to communicate with the forming machine 92. In some embodiments, the far-end electronic device 91 may be omitted.

Figure 4:
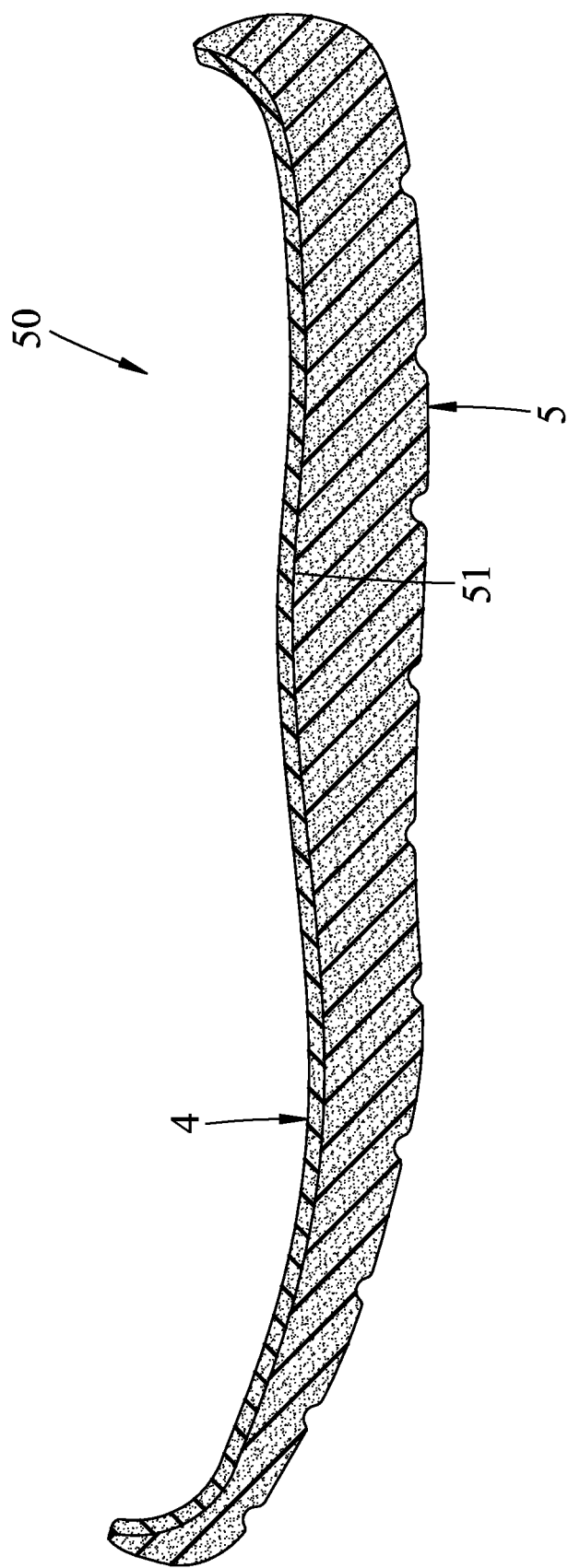
FIG. 4 is a cross-sectional view of a footwear object that is produced with the method according to an embodiment of the disclosure.
Figure 5:
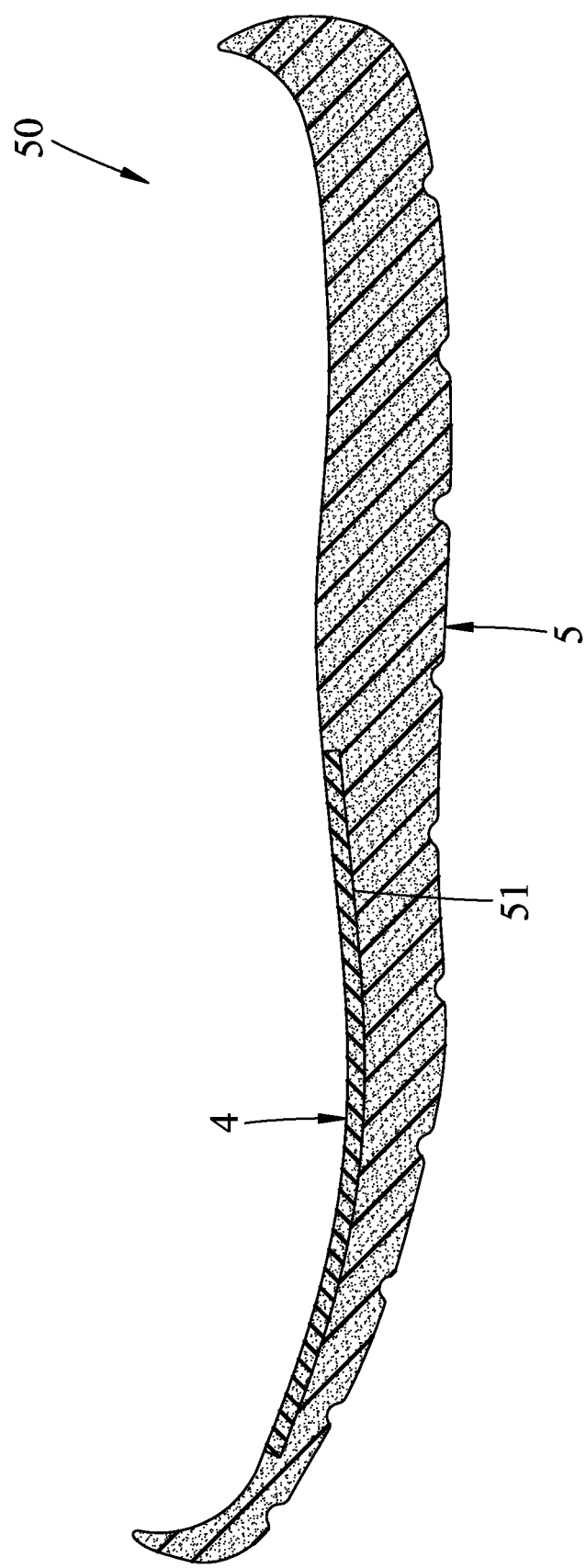
FIGS. 5-8 are cross-sectional views, illustrating different footwear objects that are produced with the method according to embodiments of the disclosure.
Figure 6:
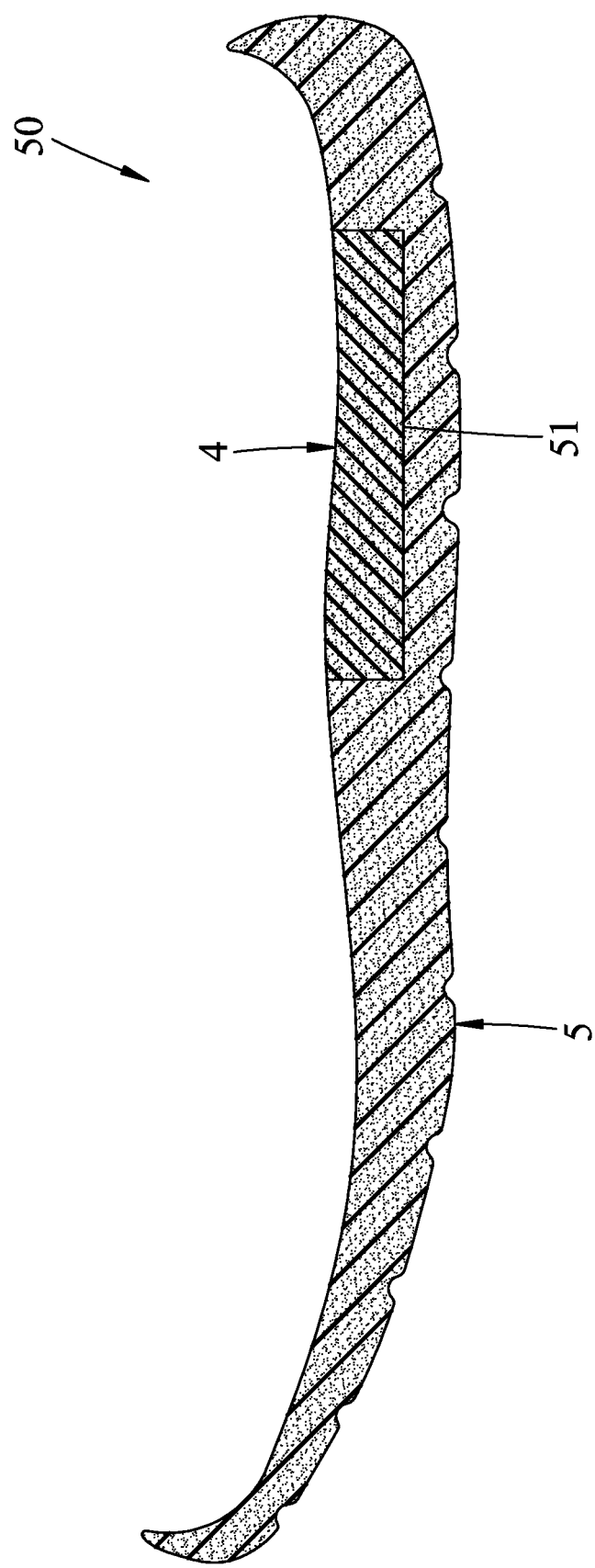
Figure 7:
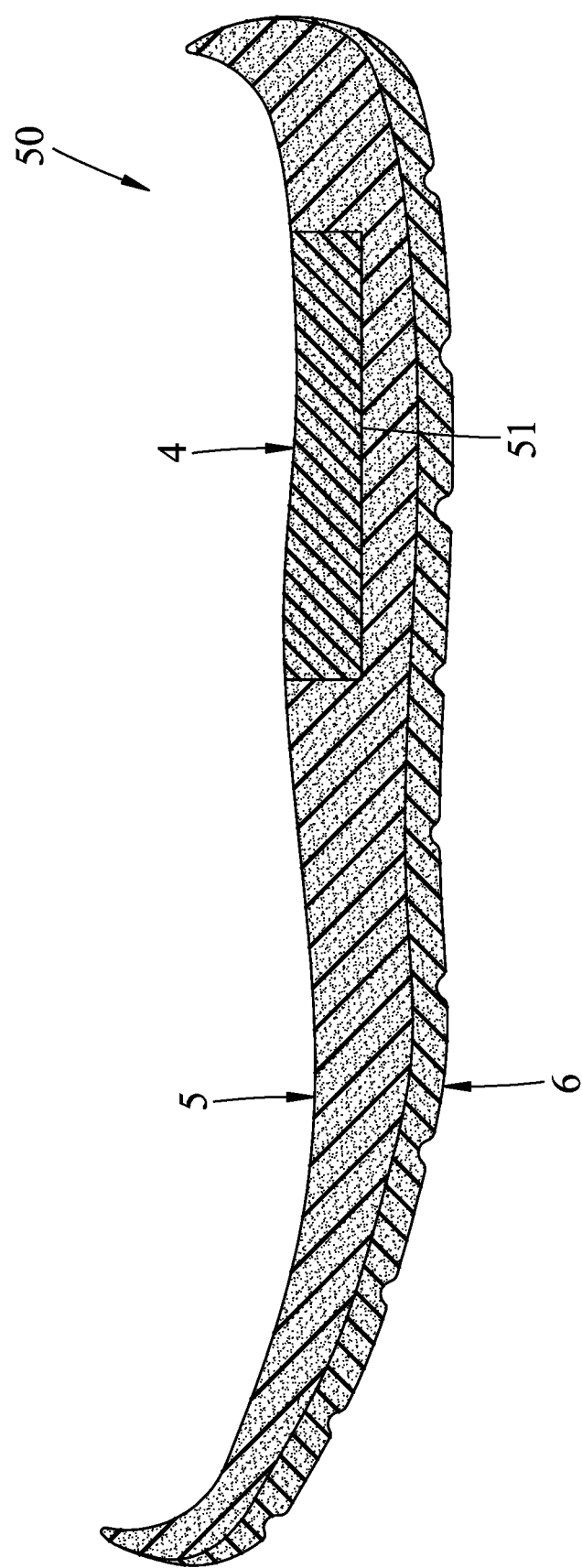
Figure 8:
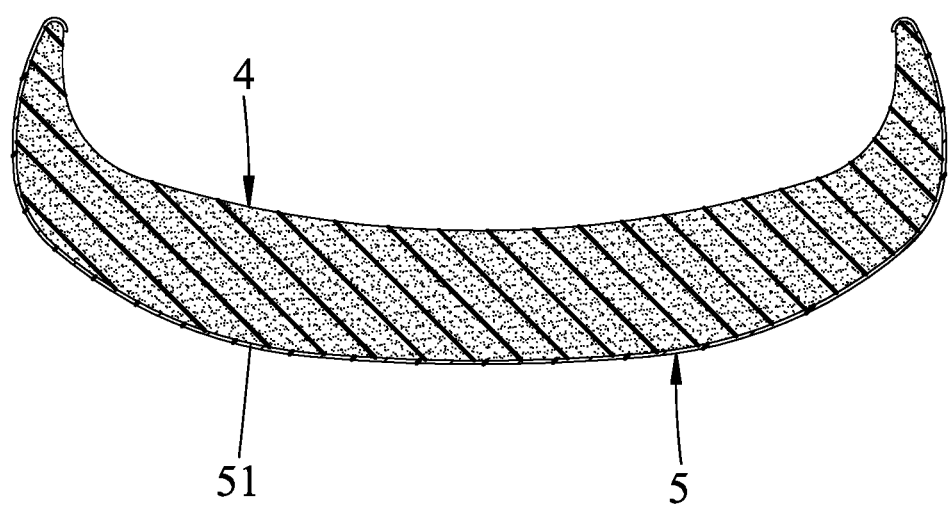

Further referring to FIGS. 4 to 8, the footwear object 50 is customized for a wearer, and has a substrate 5 and a cushion 4. The substrate 5 may be an outsole (as shown in FIGS. 4, 5 and 6), a midsole (as shown in FIG. 7) or a insole (as shown in FIG. 8) of a shoe, and defines a space 51. The cushion 4 is embedded in the space 51 of the substrate 5. In other embodiments, the footwear object 50 may have a plurality of cushions 4, and the substrate 5 may be in a form that defines a plurality of spaces 51 accordingly. FIGS. 5-8 respectively show different footwear objects 50 that are produced with the method according to an embodiment of this disclosure, and the cushions 4 of the footwear objects 50 are embedded at different positions and have different shapes.

In one embodiment, the near-end electronic device 20 includes a storage 21 that stores an application for ordering the footwear object 50, a processor 22 that is configured to execute the application to perform the method for determining a design of a customized footwear object, and an input unit 23 that is connected to the processor 22. The method includes the following steps.

In step 301, the near-end electronic device 20 receives, via the input unit 23, a user input of a requirement data set regarding features that are related to the wearer. Specifically, the requirement data set is inputted by a user when ordering the footwear object 50, and includes at least one of a weight value, a height value, a body mass index (BMI) value, a foot type (such as flat arch or high arch), a foot size or a walking profile (such as pronation or supination) of the wearer, a type of activity that the wearer intends to wear the footwear object 50 to perform (such as jogging, sprinting, playing badminton, playing basketball, mountain climbing, etc.), or a preference of the wearer for the footwear object 50 (such as softer or harder footwear object, etc.).

In another embodiment, the near-end electronic device 20 further receives a selection of a material and a type for the substrate 5 of the footwear object 50. In other embodiments, the material and the type for the substrate 5 of the footwear object 50 is predetermined. The material for the substrate 5 may be plastic, rubber, polyurethane (PU), thermoplastic polyurethane (TPU), ethylene-vinyl acetate (EVA), nylon elastomer or a combination thereof. In some embodiments, the material for the substrate 5 is a fiber material or elastic composite material. The type for the substrate 5 may include various forms as shown in FIGS. 4-8.

In step 302, the near-end electronic device 20 obtains, via a look-up table (LUT) stored in a database (e.g., the storage 21) for example, a cushion data set for producing the cushion 4 of the footwear object 50 based on the requirement data set. The cushion data set includes data regarding a position of the cushion 4, data regarding a shape of the cushion 4, data regarding a material of the cushion 4, and data regarding a hardness of the cushion 4. In some embodiments where the footwear object 50 needs to have a plurality of cushions 4, the cushion data set further includes a number of the cushions 4 and the respective position, material and hardness for each of the cushions 4. The material of the cushion 4 may be polyurethane foam, silicone, emulsion or a combination thereof. In some embodiments, the cushion 4 may be in a form of an air cushion. In some embodiments, the material for the cushion 4 may be in a form of gel.

Taking obtaining the data regarding the hardness of the cushion 4 as an example, the near-end electronic device 20 should determine a value of density of the cushion 4 based on the requirement data set, and calculate a value of volume of the cushion 4 with a given value of weight of the cushion 4 based on the value of density. Alternatively, the near-end electronic device 20 may calculate a value of weight of the cushion 4 with a given value of volume of the cushion 4 based on the value of density.

In step 303, the near-end electronic device 20 generates an order for production of the footwear object 50. The order includes the cushion data set and indicates the material and the type of the substrate 5 of the footwear object 50.

In other embodiments, rather than having the near-end electronic device 20 generate the order, the cushion data set and the material and the type of the substrate 5 are transmitted to the far-end electronic device 91 first, and the order is then generated by the far-end electronic device 91.

In step 304, the near-end electronic device 20 provides the order to the forming machine 92 through the far-end electronic device 91. Specifically, the near-end electronic device 20 transmits the order to the far-end electronic device 91. The far-end electronic device 91 further obtains information related to a required mold based on the order. The information related to the required mold corresponds to the foot size of the requirement data set, and the cushion data set including the number of the cushions 4 and the respective position, and data regarding the shape of each cushion 4, etc. The far-end electronic device 91 then generates a barcode 81 based on the order, encoding the information related to the required mold thereinto, and outputs the barcode 81 to the forming machine 92. The barcode 81 may be printed for adhering to the mold 82 or the substrate 5. In some embodiments where the far-end electronic device 91 is omitted, the barcode may be generated by the near-end electronic device 20.

In step 305, the forming machine 92 reads the barcode and decodes the barcode to obtain the content of the order and the information related to the required mold.

Figure 3:
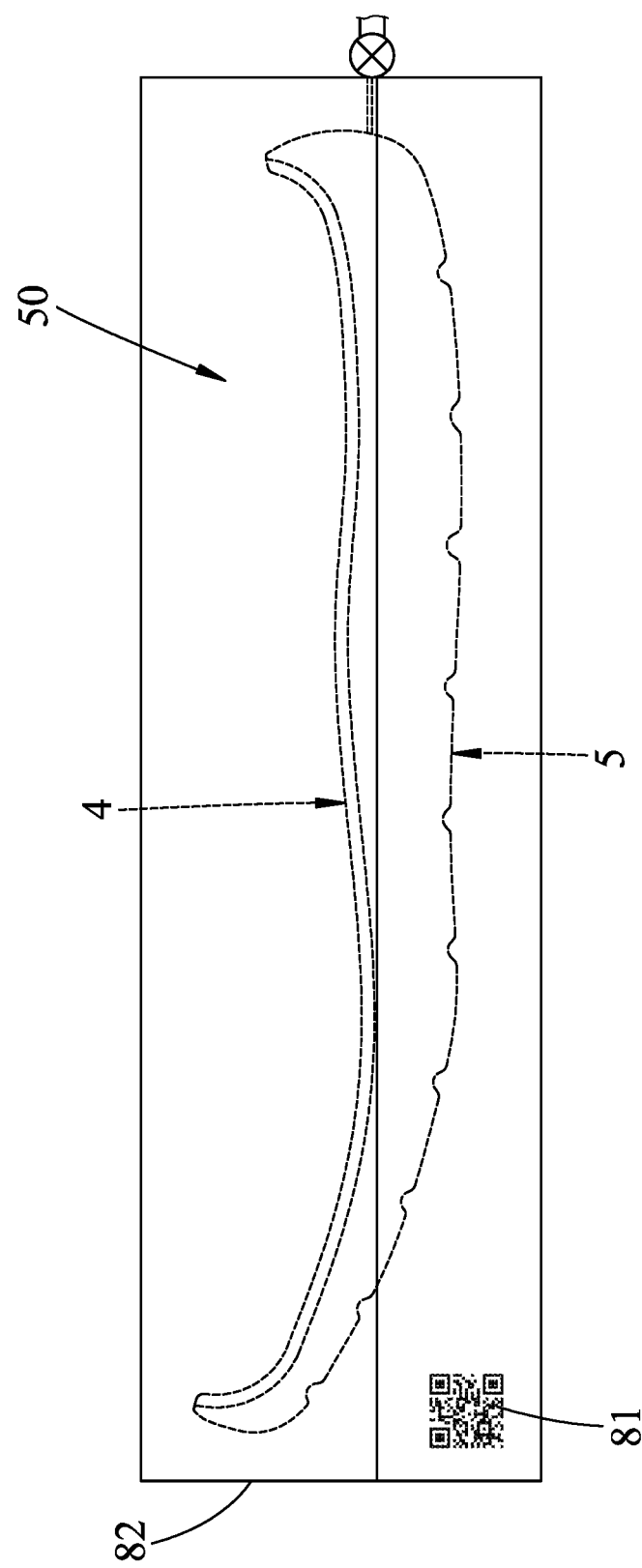
FIG. 3 is a schematic view exemplarily illustrating a mold used to form a cushion and a substrate of the customized footwear object according to an embodiment of the disclosure.

Further referring to FIG. 3, in step 306, the forming machine 92 selects a mold 82 adapted to be used to form the substrate 5 and the cushion 4 according the information related to the required mold.

In step 307, the forming machine 92, according to the order, acquires the given value of weight of the material of the cushion 4, or acquires the calculated value of weight of the material of the cushion 4.

In step 308, the forming machine 92 forms the substrate 5 using the material for the substrate 5 as indicated by the order and forms the cushion 4 according to the cushion data set in the order. Specifically, the forming machine 92 uses dual-injection molding technique to inject material into the mold 82 so as to form the cushion 4 and the substrate 5, and to have the cushion 4 embedded in the space 51 of the substrate 5. More specifically, the cushion 4 may overlap the substrate 5 as shown in FIG. 4, or the cushion 4 may be placed in a front portion of the substrate 5 as shown in FIG. 5 or in a rear portion of the substrate 5 as shown in FIG. 6, according to the data regarding the position of the cushion 4.

Figure 9:
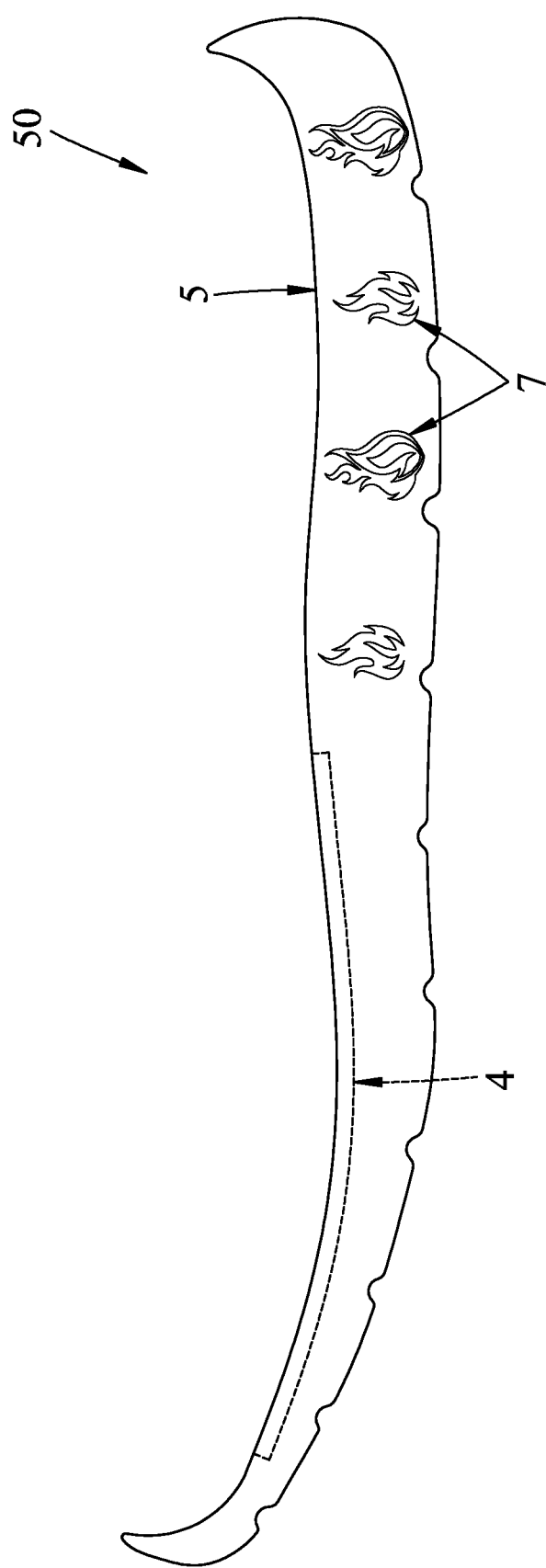
FIG. 9 is a side view exemplarily illustrating a footwear object having patterns thereon.

In other embodiments, the forming machine 92 uses 3D printing technique (e.g., use a multi-nozzle 3D printer) to form the cushion 4 and the substrate 5 individually. Moreover, the substrate 5 may further have some patterns 7 as shown in FIG. 9.

In further other embodiments, the substrate 5 is an elastic film, and in step 306, the barcode 81 is printed and adhered to the substrate 5. After the mold 82 is selected in step 306, the substrate 5 is putted in the mold 82, and the forming machine 92 forms the cushion 4 according to the cushion data set.

In summary, the cushion 4 of the footwear object 50 may be designed based on the weight, the height, the foot type, the foot size, the walking profile, the type of activity and the preference of the wearer, so that the footwear object 50 is customized for the wearer and provides relatively greater comfort and protection against shock.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for determining a design of a customized footwear object to be implemented using an electronic device executing an application for ordering the footwear object, the footwear object being customized for a wearer, and having a substrate which is an elastic film and a cushion embedded in the substrate, the method comprising steps of:
   receiving a user input of a requirement data set regarding features that are related to the wearer;
   obtaining a cushion data set for producing the cushion of the footwear object based on the requirement data set, the cushion data set including data regarding at least one of a position of the cushion, data regarding a shape of the cushion, data regarding a material for the cushion, or data regarding a hardness of the cushion;
   generating an order for production of the footwear object, the order including the cushion data set; and
   providing the order to a forming machine for the forming machine to produce the footwear object;
   wherein the step of obtaining a cushion data set includes obtaining the data regarding the hardness of the cushion by determining a value of density of the cushion based on the requirement data set, and implementing either a first calculation or a second calculation,
   wherein, in the first calculation, a value of volume of the cushion to be embedded in the substrate is calculated with a given value of weight of the cushion based on the value of density, and the data regarding the hardness of the cushion includes the value of volume of the cushion and the given value of weight of the cushion,
   wherein, in the second calculation, a value of weight of the cushion to be embedded in the substrate is calculated with a given value of volume of the cushion based on the value of density, and the data regarding the hardness of the cushion includes the value of weight of the cushion and the given value of volume of the cushion.

2. The method as claimed in claim 1, further comprising a step of receiving a selection of at least one of a material or a type for the substrate of the footwear object,
   wherein the step of generating an order for production of the footwear object includes generating the order to indicate at least one of the material or the type for the substrate of the footwear object.

3. The method as claimed in claim 1, wherein the step of receiving a requirement data set regarding features that are related to the wearer includes receiving at least one of a weight value, a height value, a foot type, a foot size or a walking profile of the wearer, a type of activity that the wearer intends to wear the footwear object to perform, or a preference of the wearer for the footwear object to serve as the requirement data set.

4. The method as claimed in claim 1, wherein the step of providing the order to a forming machine includes generating a barcode that contains content of the order, in order for the forming machine to read and decode the barcode to obtain the content of the order.

5. A method for fabricating a customized footwear object to be implemented by an electronic device executing an application for ordering the footwear object and a forming machine communicate with the electronic device, the footwear object being customized for a wearer, and having a substrate which is an elastic film and a cushion embedded in the substrate, the method comprising steps of:
   receiving, by the electronic device, a user input of a requirement data set regarding features that are related to the wearer;
   obtaining, by the electronic device, a cushion data set for producing the cushion of the footwear object based on the requirement data set, the cushion data set including at least one of data regarding a position of the cushion, data regarding a shape of the cushion, data regarding a material for the cushion, or data regarding a hardness of the cushion;
   generating, by the electronic device, an order for production of the footwear object, the order including the cushion data set;
   providing, by the electronic device, the order to the forming machine; and
   forming, by the forming machine, the substrate and the cushion according to the order, wherein the cushion is embedded in the substrate at a position according to the data regarding the position of the cushion;
   wherein the step of obtaining a cushion data set includes obtaining the data regarding the hardness of the cushion by determining a value of density of the cushion based on the requirement data set, and implementing either a first calculation or a second calculation,
   wherein, in the first calculation, a value of volume of the cushion to be embedded in the substrate is calculated with a given value of weight of the cushion based on the value of density, and the data regarding the hardness of the cushion includes the value of volume of the cushion and the given value of weight of the cushion,
   wherein, in the second calculation, a value of weight of the cushion to be embedded in the substrate is calculated with a given value of volume of the cushion based on the value of density, and the data regarding the hardness of the cushion includes the value of weight of the cushion and the given value of volume of the cushion.

6. The method as claimed in claim 5, further comprising a step of selecting at least one of a material or a type for the substrate of the footwear object,
  wherein the step of generating an order for production of the footwear object includes generating the order to indicate at least one of the material or the type for the substrate of the footwear object, and the step of forming the substrate and the cushion includes forming the substrate with the material for the substrate indicated by the order and forming the cushion according to the cushion data set in the order.

7. The method as claimed in claim 5, wherein the step of receiving a requirement data set regarding features that are related to the wearer includes receiving at least one of a weight value, a height value, a foot type, a foot size or a walking profile of the wearer, a type of activity that the wearer intends to wear the footwear object to perform, or a preference of the wearer for the footwear object to serve as the requirement data set.

8. The method as claimed in claim 5, wherein the step of providing the order includes generating a barcode that contains content of the order,
  wherein the method further comprises, before the step of forming the substrate and the cushion, steps of the forming machine reading the barcode, and the forming machine decoding the barcode to obtain the content of the order.

* * * * *